United States Patent
Lenharo (10) Patent No.: US 11,419,889 B2
(45) Date of Patent: Aug. 23, 2022

(54) ORAL COMPOSITIONS FOR POST-DENTAL IMPLANTS

(71) Applicant: Ariel Lenharo, Hollywood, FL (US)

(72) Inventor: Ariel Lenharo, Hollywood, FL (US)

( * ) Notice: Subject to any disclaimer, the term of this patent is extended or adjusted under 35 U.S.C. 154(b) by 0 days.

(21) Appl. No.: 17/096,856

(22) Filed: Nov. 12, 2020

(65) Prior Publication Data

US 2022/0143073 A1    May 12, 2022

(51) Int. Cl.
| | | |
|---|---|---|
| *A61K 31/728* | (2006.01) | |
| *A61P 31/02* | (2006.01) | |
| *A61K 9/00* | (2006.01) | |
| *A61K 31/695* | (2006.01) | |
| *A61K 36/82* | (2006.01) | |
| *A61K 47/10* | (2017.01) | |
| *A61K 47/18* | (2017.01) | |
| *A61K 47/20* | (2006.01) | |
| *A61K 47/26* | (2006.01) | |
| *A61K 47/32* | (2006.01) | |
| *A61K 47/38* | (2006.01) | |

(52) U.S. Cl.
CPC .......... *A61K 31/728* (2013.01); *A61K 9/0053* (2013.01); *A61K 31/695* (2013.01); *A61K 36/82* (2013.01); *A61K 47/10* (2013.01); *A61K 47/183* (2013.01); *A61K 47/20* (2013.01); *A61K 47/26* (2013.01); *A61K 47/32* (2013.01); *A61K 47/38* (2013.01); *A61P 31/02* (2018.01)

(58) Field of Classification Search
CPC .. A61K 31/728; A61K 9/0053; A61K 31/695; A61K 36/82; A61K 47/10; A61K 47/183; A61K 47/20; A61K 47/26; A61K 47/32; A61K 47/38; A61P 31/02
See application file for complete search history.

(56) References Cited

U.S. PATENT DOCUMENTS

| | | | | |
|---|---|---|---|---|
| 2004/0254143 | A1* | 12/2004 | Mastradonato | A61K 9/7015 514/54 |
| 2008/0025926 | A1* | 1/2008 | Kavouklis | A61K 8/4926 424/53 |
| 2008/0095719 | A1* | 4/2008 | Herrmann | A61P 43/00 424/48 |
| 2009/0156563 | A1* | 6/2009 | Baschong | A61Q 19/08 514/159 |

FOREIGN PATENT DOCUMENTS

| | | | | |
|---|---|---|---|---|
| WO | WO-9912517 A1 * | 3/1999 | | A61K 8/8176 |
| WO | WO-2016065443 A1 * | 5/2016 | | A61K 8/43 |

OTHER PUBLICATIONS

English translation of WO-2016065443-A1 from Google Patents. Retrieved on Dec. 4, 2021, pp. 1-9. (Year: 2021).*

* cited by examiner

*Primary Examiner* — Doan T Phan
(74) *Attorney, Agent, or Firm* — Intellectual Property Law Group LLP

(57) ABSTRACT

Oral compositions generally, but not exclusively, used for post dental implants that provide low abrasiveness and improved sanitization and protection of dental implants as well as facilitation of tissue regeneration with better active stability and compatibility as well as synergistic effects are described. The oral compositions include one or more mucus regenerators, one or more antiseptic agents, and one or more orally acceptable carrier actives selected from a group of one or more thickeners, one or more humectants, one or more sweeteners, a preservative, one or more surfactants, a film forming agent, a thixotropic agent, a solubilizing agent, a chelating agent, a coloring agent, an anti-tartar agent, an abrasive, an antioxidant agent, a flavoring agent, and a water vehicle, or mixtures thereof.

14 Claims, 1 Drawing Sheet

ORAL COMPOSITIONS FOR POST-DENTAL IMPLANTS

FIELD OF INVENTION

The present invention refers to oral compositions usually used for the sanitization and protection of dental implants as well as for the facilitation of tissue regeneration.

BACKGROUND OF THE INVENTION

The formulation of specific products for sanitizing and protecting dental implants as well as for facilitating tissue regeneration is intended to be a tool that enables dental surgeons and professionals to achieve its results in a simple manner without, however, changing the concept of oral hygiene.

Oral hygiene for post-dental implants is of extreme importance and, thus, cannot be possibly neglected. As in the case of natural teeth, implanted teeth require careful sanitation as they are subject to the formation of bacterial plaque and oral infections that reflect health in general. While polishing, plaques are also formed in the implants and, for this reason, the proper hygiene of the teeth is important. Thus, oral hygiene is directly related to periodontal health and, consequently, increased longevity of dental implants.

Mouthwashes have been used in the chemical control of the bacterial plaque and as substitutes or adjuncts to mechanical procedures, besides being facilitators in the delivery of active compounds in the treatment of specific infections. However, mouthwashes in no case must be substituted for the mechanical methods of plaque removal, and thus, act as auxiliaries thereof. Thus, mouthwashes represent the simplest means for the delivery of antiseptic substances. Structurally, an oral composition for this purpose has a formulation like the basic wash/rinse compositions: antiseptic, moisturizer, surfactant, water and flavoring.

Likewise, dentifrices are formulations that gather several fundamental substances with thickening, abrasive, wetting, preservative, sweetener, flavoring and foaming purposes, in addition to water. Dentifrices can be in the form of dental cream and dental gels and have broad and recognized purposes by dental professionals and consumers. The main purposes and uses of dentifrices include the cleaning of the mouth, including soft teeth and tissues, polishing the restorations and teeth, removing debris and bacterial plaque, and preventing periodontal diseases and dental cavities.

Basic dentifrice compositions usually include a thickener, which may be one or more gel-forming substances such as cellulose derivatives, guar and xanthan gums and thickening silicas; an abrasive agent including insoluble substances such as calcium carbonate and calcium phosphate, zirconium silicate, alumina and abrasive silica; surfactants such as sodium lauryl sulfate (SLS), sodium lauroyl sarcosinate (INCI), poloxamer or cocamidopropyl betaine (CAPB); wetting agents such as glycerin, sorbitol, propylene glycol or polyethylene glycol 400; and sweeteners such as saccharin, cyclamate, stevia and xylitol. The basic dentifrice compositions also include various flavorings, as well as preservatives such as parabens and benzoates. Dyes and agents for therapeutic purposes are of optional use.

These types of formulations provide researchers with a wide range of possibilities in the creation of oral compositions with the most varied applications ranging from simple cosmetic purposes to completely therapeutic uses.

For dentifrices, numerous credits have been given that mimic their indication insofar as the expectations grow in preserving, protecting, treating hard and soft tissues of the mouth and, currently, caring with the implants. In this respect, osteo-integrated-type metal implants have sparked concerns because they require, in addition to hygiene, protection and the due treatment of the gingiva. Oral compositions for multiple, but specific, purposes must first conform to the formulation item to meet the specificity: in addition to sanitization, attenuation of inflammation, promotion of healing and protection to the surgical wound. Considering that titanium is the most used metal in osteo-integrated-type metal implants, the dentifrice must not have fluorine as it can attack its surface.

Respecting the limits for the inclusion of agents for therapeutic purposes and in order to have safe and efficient action, the formulation is completed in a manner when it contributes to the effectiveness of the dentifrice without interfering with its specificity. Thus, selection of the components of the dentifrice must be judicious, providing the perfect action of all actives, synchronously implementing activities that combine and complement the brushing, preferably with a soft or extra-soft brush. Various substances have been used in dentifrices for different purposes: anticaries, anti-tartar, anti-gingivitis, and the like, and in some cases acting together. Triclosan, cetylpyridinium chloride, sodium pyrophosphate, potassium citrate and zinc chloride are examples of these substances that act synergistically in some products, characterized as broad-spectrum dentifrices.

Following technological development and on top of meeting the expectations and needs of the dental practitioner, a dentifrice has been developed with specificity for sanitization, protection and tissue repair for the case of metal implants placed in the mouth, with safe and efficient inputs. Accordingly, in order to achieve the objectives of an oral composition with these properties and suitable for the intended usage by the dental practitioner, these substances have been harmonically incorporated into a base of gel-type and cream-type dentifrices in which various components as a whole have an efficient action in the sanitization, protection, and faster repair of tissues, ensuring good oral composition performance and stability.

Likewise, in the case of mouthwashes, in order to achieve these same specific objectives, in the case of sanitizing dental implants, selected substances as a function of special features have been chosen to better meet these needs. The substances to be added in the formulation of the present invention are not common in the conventional rinses since the purpose of the rinse in question is especially developed for implanted teeth.

In short, there is a need for novel oral compositions generally, but not exclusively, used for post dental implants that provide low abrasiveness and improved sanitization and protection of dental implants as well as facilitation of tissue regeneration.

SUMMARY

The present invention relates to oral compositions generally, but not exclusively, used for post dental implants that provide low abrasiveness and improved sanitization and protection of dental implants as well as facilitation of tissue regeneration with better active stability and compatibility as well as synergistic effects.

The oral compositions of the present invention comprise one or more mucus regenerators, one or more antiseptic agents, and one or more orally acceptable carrier actives selected from a group of one or more thickeners, one or more humectants, one or more sweeteners, a preservative, one or more surfactants, a film forming agent, a thixotropic agent, a solubilizing agent, a chelating agent, a coloring agent, an anti-tartar agent, an abrasive, an antioxidant agent, a flavoring agent, and a water vehicle, or mixtures thereof.

DETAILED DESCRIPTION OF THE INVENTION

While the specification concludes with claims that particularly point out and distinctly claim the invention, it is believed the present invention will be better understood from the following description.

Definitions

The term "orally acceptable carrier" as used herein means a suitable vehicle or ingredient, which can be used to form and/or apply the present compositions to the oral cavity in a safe and effective manner. The orally acceptable carrier is not harmful to a mammal in amounts disclosed herein when retained in the mouth, without swallowing, for a period enough to permit effective contact with a dental surface as required herein. Suitable orally acceptable carriers include, for example, one or more of the following: water, a thickener, a humectant, a surfactant, an abrasive, a sweetener, a flavoring, a coloring agent, an anti-caries agent, an antibacterial, agent, a preservative, a chelating agent, and mixtures thereof.

The term "comprising" as used herein means that ingredients other than those specifically mentioned can be added. This term encompasses the terms "consisting of" and "consisting essentially of." The compositions of the present invention can comprise, consist of, and consist essentially of the essential elements and limitations of the invention described herein, as well as any of the additional or optional ingredients, or limitations described herein.

The term "effective amount" as used herein means an amount of a compound or composition sufficient to induce a positive benefit, an oral health benefit, and/or an amount low enough to avoid serious side effects, i.e., to provide a reasonable benefit to risk ratio, within the sound judgment of someone of ordinary skill in the art.

The term "oral composition" as used herein means a product that in the ordinary course of usage is retained in the oral cavity for a time sufficient to contact some or all of the dental surfaces and/or oral tissues for purposes of oral activity. The oral composition of the present invention may be in various forms including mouthwash, dentifrice, toothpaste, tooth gel, tooth powder, non-abrasive gel, subgingival gel, petrolatum gel, mousse, foam, mouth spray, lozenge, lipstick, prophy paste, chewing gum, oral tablet, sponge, floss, or dental implement. The oral composition may also be incorporated onto strips or films for direct application or attachment to oral surfaces or incorporated into floss.

The term "dentifrice" as used herein refers to a product, which in the ordinary course of administration, is not intentionally swallowed for purposes of systemic administration of particular therapeutic agents, but is rather retained in the oral cavity for a time sufficient to contact substantially all of the tooth surfaces and/or oral tissues for purposes of oral activity. A dentifrice of the present invention may be in the form of a toothpaste or dentifrice. The term "dentifrice," as used herein, also means paste or gel formulations unless otherwise specified. The dentifrice may be in any desired form, such as deep striped, surface striped, multi-layered, having the gel surrounding the paste, or any combination thereof.

The term "teeth" as used herein refers to natural teeth as well as artificial teeth or dental prosthesis.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. The term "weight percent" may be denoted as "wt. %" herein.

The present invention relates to oral compositions generally, but not exclusively, used for post dental implants that provide low abrasiveness and improved sanitization and protection of dental implants as well as facilitation of tissue regeneration with better active stability and compatibility as well as synergistic effects.

The oral compositions of the present invention comprise one or more mucus regenerators, one or more antiseptic agents, and one or more orally acceptable carrier actives selected from a group of one or more thickeners, one or more humectants, one or more sweeteners, a preservative, one or more surfactants, a film forming agent, a thixotropic agent, a solubilizing agent, a chelating agent, a coloring agent, an anti-tartar agent, an abrasive, an antioxidant agent, a flavoring agent, and a water vehicle, or mixtures thereof.

The oral compositions of the present invention include one or more mucus regenerators. One of these mucus regenerators may also have antiseptic properties. The incorporation of a mucus regenerator with antiseptic properties broadens the possibilities of a novel active ingredient in an oral composition for the primary and main purpose of regenerating gingival tissue markedly and possibly accelerating the curing or regeneration process. The mucus regenerator with antiseptic properties active ingredient may be silanol salicylate. Silanol salicylate may be commercially available as D.S.B.C.®. Silanol salicylate is an organic silicon used in oral care products with beneficial properties on the mucosa including regenerative, anti-inflammatory and cell renewal action; teeth aid remineralization by forming an ideal connective tissue; and atrophy prevention on the bone structure. Another one of these mucus regenerators may have anti-inflammatory properties. The mucus regenerator with anti-inflammatory property may be hyaluronic acid. Hyaluronic acid is a natural body protein that facilitates healing and regeneration of tissues with anti-inflammatory properties. Studies demonstrate that it has dental use in the treatment of gingivitis. In preferred embodiments, the oral compositions may comprise about 0.05 weight % to about 0.55 weight % of one or more mucus regenerators, e.g. about 0.05 weight % of hyaluronic acid. In some other embodiments, the oral compositions may comprise additionally about 0.50 weight % of silanol salicylate.

The oral compositions of the present invention include an antioxidant and antiseptic agent with anti-inflammatory properties. The antioxidant and antiseptic agent with anti-inflammatory properties may be a plant extract, in this case, green tea extract (*Camellia sinensis*). The green tea extract has shown the ability to sanitize and maintain an operated area from being susceptible to inflammation, as well as contaminants and infections. In preferred embodiments, the oral compositions may comprise about 0.50 weight % of antioxidant and antiseptic agent with anti-inflammatory properties, e.g. about 0.50 weight % of green tea extract.

The oral compositions of the present invention include one or more thickeners. The thickener is innocuous with strong bonds to maintain the stability of the oral composition within its shelf-life but fragile to the extent that it can release actives during brushing. Thus, the rheological characteristics of the oral compositions comprising one or more thickeners and in this embodiment are fundamental. In this respect and seeking compatibility with the actives and good associated performance, the thickener of the oral compositions of the present invention include carboxymethyl cellulose and Tixosil® 43B, a white finely controlled milled silica powder with standard thickening capabilities and a high oil absorption which is also a thixotropic agent. In preferred embodiments, the oral compositions may comprise about 1.00 weight % to about 11.20 weight % of one or more thickeners, e.g. about 1.00 to about 1.20 weight % of carboxymethyl cellulose and about 10.00 weight of Tixosil® 43B.

The oral compositions of the present invention include an abrasive. An abrasive removes debris and surface stains. The abrasive agent may be Tixosil® 73, a type of hydrated abrasive silica, which has low abrasiveness so that there are no risks on the surface of the implant or even the removal of the surface oxide layer, which configures the biologically compatible character. The oral compositions of the present invention also include a film forming agent which together with Tixosil® 73, aids in sanitization. The film forming agent may be polyvinylpyrrolidone K30. In some embodiments, the oral compositions may comprise about 5.00 weight % to about 10.00 weight % of the abrasive agent, e.g. about 5.00 to about 10.00 weight % of Tixosil® 73. In preferred embodiments, the oral compositions may comprise about 0.50 weight % of the film forming agent, e.g. about 0.50 weight % of polyvinylpyrrolidone K30. In this way, sanitization and surface protection of the implants are assured.

The oral compositions of the present invention include an anti-cariogenic agent. The anti-cariogenic agent may be a polysaccharide. The polysaccharide capable of anti-cariogenic action is xylitol due to its nature of not being fermented by the *Streptococcus mutans* bacteria. In preferred embodiments, the oral compositions comprise about 0.50 weight % of the anti-cariogenic agent, e.g. about 0.50 weight % of xylitol.

The oral compositions of the present invention include one or more humectants. A humectant keeps oral compositions from hardening upon exposure to air. Certain humectants may also impart desired sweetness or flavor to oral compositions. The one or more humectants included in the oral compositions of the present invention may be glycerin which serves as a wetting agent in order to prevent drying. The one or more humectants may also be sorbitol. In preferred embodiments, the oral compositions comprise about 5.00 to about 65.00 weight % of humectants, e.g. about 5.00 to about 40.00 weight % of glycerin and about 60.00 weight % of sorbitol.

The oral compositions of the present invention include one or more surfactants. From the nature of the application and use of the oral compositions of the present invention on the areas affected by the clinical situation (post-implant), one of the surfactants needs to be smooth and is a non-ionic tensioactive and, thus, may be lauryl glucoside. This surfactant enables high cleaning capacity on top of not interacting with the other formulation active ingredients. Another one of the surfactants that may be used is an ionic tensioactive embodied in lauryl sodium sulfate. In preferred embodiments, the oral compositions may comprise about 0.50 to 2.00 weight % of surfactants, e.g. about 1.50 weight % of lauryl glucoside and about 0.50 weight % of lauryl sodium sulfate.

The oral compositions of the present invention include a preservative. The preservative may be sodium benzoate. In preferred some embodiments, the oral compositions may comprise about 0.30 weight % of preservative, e.g. about 0.30 weight % of sodium benzoate.

The oral compositions of the present invention include one or more sweeteners. The one or more sweeteners may be saccharin. The one or more sweeteners may also be xylitol. In preferred embodiments, the oral compositions may comprise about 0.05 to about 0.60 weight % of preservatives, e.g. about 0.05 to about 0.10 weight % of saccharin and about 0.50 weight % of xylitol.

The oral compositions of the present invention include a solubilizing agent. The solubilizing agent may be hydrogenated Ricinus oil (Castor Oil). In preferred embodiments, the oral compositions may comprise about 2.00 weight % of solubilizing agent, e.g. about 2.00 weight % of hydrogenated Ricinus oil.

The oral compositions of the present invention include a chelating agent. The chelating agent may be ethylenediaminetetraacetic acid (EDTA). In preferred embodiments, the oral compositions may comprise about 0.05 weight % of chelating agent, e.g. about 0.05 weight % of ethylenediaminetetraacetic acid.

The oral compositions of the present invention optionally include a coloring dye. The coloring dye may be titanium dioxide. In preferred embodiments, the oral compositions may comprise about 1.00 weight % of coloring dye, e.g. about 1.00 weight % of titanium dioxide.

The oral compositions of the present invention optionally include an anti-tartar agent. The anti-tartar agent may be tetrasodium pyrophosphate. In preferred embodiments, the oral compositions may comprise about 0.50 weight % of anti-tartar agent, e.g. about 1.00 weight % of tetrasodium pyrophosphate.

The oral compositions of the present invention optionally include a flavoring. The flavoring may be mint aroma. In preferred embodiments, the oral compositions may comprise about 0.30 to 0.60 weight % of flavoring, e.g. about 0.30 to 0.60 weight % of mint aroma.

The oral compositions of the present inventions include water. Water employed in the preparation of the oral compositions of the present invention may be purified and may make up the balance of the oral compositions. In preferred embodiments of the present invention, the oral compositions may comprise about 11 to about 73 weight % of purified water. This amount of water may include the free water which added plus the amount which is introduced with other components of the oral composition, such as with sorbitol.

The oral compositions of the present invention is suitable to be used and associated with a condition selected from the group consisting of: tooth loss, oral surgery, endodontic pathoses, stomatitis, alveolar bone resorption, lesions, gingivitis, periodontitis, tobacco induced disease, and combinations thereof.

NON-LIMITING EXAMPLES

The oral compositions illustrated in the following examples illustrate specific and preferred embodiments within the scope of the present invention. These examples are given solely for the purpose of illustration and are not to be construed as limitations of the present invention as many variations of the invention are possible and can be undertaken by someone of ordinary skill in the art without departing from its spirit or scope. Unless otherwise indicated, all ingredients are expressed as a weight percentage of the composition.

A laboratory study was carried out to evaluate the effect of different vehicles of oral hygiene of the exemplary oral compositions of the present invention on the periimplant clinical parameters. In this study, 32 patients with a total of 187 implants used one of the vehicles tested in the exemplary oral compositions of the present invention directed to 1) dentifrice (dental cream), Example A; 2) dental gel, Example B, and 3) mouthwash, Example C. The patients who received the exemplary gel or dentifrice oral compositions of the present invention experienced a partial fixed rehabilitation supported by implants, while patients submitted to the use of the exemplary mouthwash oral composition of the present invention experienced full-arch fixed prosthesis supported by dental implants. Patients were submitted to the clinical analysis on the implants at the baseline and after 10 days of the beginning of the use of the exemplary oral compositions of the present invention. The probing depth, level of the peri-implant mucosa, distance from the implant platform to the bottom, the peri-implant pocket sulcus, the gingival inflammation index and the visible plaque index in each of the 6 sites were evaluated. In general, all the exemplary oral compositions of the present invention showed to be safe for use with no signs of side effect, and a reduction of the biofilm index and inflammation have been noted, with alteration at the periimplant mucosa marginal level due to the reduction of the inflammation. Different vehicles of the exemplary oral compositions of the present invention were able to reduce the biofilm accumulation and the inflammation around the dental implants with safety in a short-term evaluation period.

Material and Methods

General Procedures, Eligible Criteria, and Laboratory Test Design 3 types of vehicles of the exemplary oral compositions of the present invention were tested (dentifrice, dental gel, and mouthwashes). The dentifrice and gel were tested in patients that presented partial fixed prothesis supported by dental implants, while the mouthwash was tested in patients with a total fixed prothesis supported by dental implants. Thirty two patients were evaluated before and after 10 days of the professional biofilm control that consists in the removal of the screwed protheses, the execution of the peri-implants analysis, scaling and polishing of the implants and prosthesis. All these patients presented more than one year after the last maintenance visit, and all of then presented the diagnosis of mucositis. All the patients were instructed regarding the oral hygiene procedure and the using of the products during the whole time of the experimental procedure.

The patients included in this laboratory test study required patients to have dental implants undergoing partial or total rehabilitation with permanent prostheses installed for at least 12 months, within the age range of 18 to 60 years, and systemically healthy. Smoking, decompensated diabetics and patients with a history of radiotherapy or chemotherapy were excluded from the laboratory study.

The exemplary oral compositions of the present invention used in the laboratory test study had the following formulations:

Example A—Gel

| Active Ingredient | Function |
| --- | --- |
| Carboximetilcelullose | Thickener |
| Glycerin | Humectant |
| Sorbitol | Humectant |
| Sodium Benzoate | Preservative |
| Xilitol | Sweetener/Anticavity |
| Lauryl Glucoside | Nonionic Tensoactive |
| Sodium Lauryl Sulfate | Anionic Tensoactive |
| Hyaluronic Acid | Mucus Regenerator |
| Polyvinylpyrrolidone K30 | Film Forming Agent |
| Dimethyl silanediol salicylate | Antiseptic and Mucus Regenerator |
| Tixosil ® 43 B | Thickener and Thixotropic Agent |
| Tixosil ® 73 | Abrasive |
| Tetrasodium pyrophosphate | Anti-tartar |
| Saccharin | Sweetener |
| Camelia Sinensis (Green Tea Extract) | Antioxidant, Antiseptic |
| Hydrogenated Ricinus Oil (Castor Oil) | Solubilizer, Solubilizing Agent |
| Mint Aroma | Flavoring |
| EDTA | Chelating Agent |
| Blue Dye Cl42090 | Colorant |
| Yellow Dye Cl19140 | Colorant |
| Purified Water | Vehicle |

Example B—Dentrifice (Dental Cream)

| Active Ingredient | Function |
| --- | --- |
| Carboximetilcelullose | Thickener |
| Glycerin | Humectant |
| Sodium Benzoate | Preservative |
| Xilitol | Sweetener/Anticavity |
| Lauryl Glucoside | Nonionic Tensoactive |
| Sodium Lauryl Sulfate | Anionic Tensoactive |
| Hyaluronic Acid | Mucus Regenerator |
| Titanium Dioxide | Coloring |
| Polyvinylpyrrolidone K30 | Film Forming Agent |
| Dimethylsilanediol salicylate | Antiseptic and Mucus Regenerator |
| Tixosil ® 43 B | Thickener and Thixotropic Agent |
| Tixosil ® 73 | Abrasive |
| Tetrasodium pyrophosphate | Anti-tartar |
| Saccharin | Sweetener |
| Camelia Sinensis (Green Tea Extract) | Antioxidant, Antiseptic |
| Hydrogenated Ricinus Oil (Castor Oil) | Solubilizer, Solubilizing Agent |
| Mint Aroma | Flavoring |
| EDTA | Chelating Agent |
| Purified Water | Vehicle |

Example C—Mouthwash

| Active Ingredient | Function |
| --- | --- |
| Glycerin | Humectant |
| Sodium Benzoate | Preservative |
| Xilitol | Sweetener/Anticavity |
| Lauryl Glucoside | Nonionic Tensoactive |
| Sodium Lauryl Sulfate | Anionic Tensoactive |
| Hyaluronic Acid | Mucus Regenerator |
| Polyvinylpyrrolidone K30 | Film Forming Agent |
| Dimethylsilanediol salicylate | Antiseptic and Mucus Regenerator |

-continued

| Active Ingredient | Function |
| --- | --- |
| Tetrasodium pyrophosphate | Anti-tartar |
| Saccharin | Sweetener |
| Camelia Sinensis (Green Tea Extract) | Antioxidant, Antiseptic |
| Hydrogenated Ricinus Oil (Castor Oil) | Solubilizer, Solubilizing Agent |
| Mint Aroma | Flavoring |
| EDTA | Chelating Agent |
| Blue Dye Cl42090 | Colorant |
| Yellow Dye Cl19140 | Colorant |
| Purified Water | Vehicle |

Clinical Evaluation 6 sites per implant (mesio-buccal, buccal, disto-buccal, mesio-palatine-lingual, palatine/lingual, disto-palatine/lingual) were analyzed before and after 10 days of the professional biofilm control and the beginning of the use of the exemplary oral compositions of the present invention tested in this test laboratory study: 1) Probing Depth (PB): Distance from the periimplant/gingival margin to the bottom of the periimplant/periodontal sulcus/pocket; 2) Periimplant mucosal marginal level (PML): Distance from the periimplant mucosal/gingival margin to the bottom of the periimplant/periodontal sulcus/pocket; 3) Clinical attachment level (CAL): Distance from the enamel-cemetum junction or implant platform to the to the bottom of the periimplant/periodontal sulcus/pocket; 4) Inflammation Index of Loe & Silness, 1963 (II): Score 0—Absence of inflammation; Score 1: Mild inflammation—slight color change in the gingival margin associated with a small change in soft tissue texture; Score 2: Moderate inflammation—marginal soft tissue with an aspect of vitrification, redness, edema and hypertrophy; Score 3: Severe inflammation—abundant redness or hypertrophy associated with spontaneous bleeding; 5) Biofilm Index of Silness & Loe 1964 (BI): Score 0—Absence of biofilm; Score 1: Biofilm detected only by probing; Score 2: Moderate presence of visible biofilm; Score 3: Abundant presence of visible biofilm of formation of dental calculus Statistical Analysis All the data presented a normal distribution. Then, the paired t-test was used to compare the initial and final values of the clinical attachment level, Gingival/mucosal marginal level, probing depth, inflammation and biofilm index. All statistical tests used in the laboratory test study were applied at the 5% significance level. The software GraphPad Prism 6 (San Diego, Calif., USA) was used to perform the statistical analysis.

Results

Figure 1:
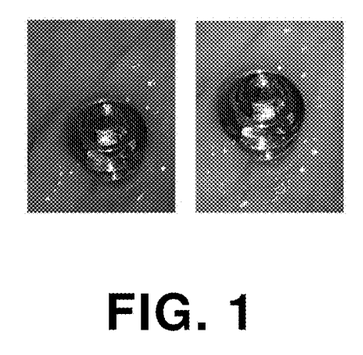
FIG. 1 shows the clinical aspect at the baseline (left) and after (right) the use for 10 days of an exemplary dentrifice oral composition of the present invention.

Dentifrice 10 patients were treated with partial fixed prothesis supported by implants. These patients had a total of 48 implants. Only one patient experienced a baseline CAL of 3 mm (patient 2). It was showed that all the patients experienced a reduction in the BI and II, except patient number 4. In general, the use of the exemplary dentifrice oral composition of the present invention was associated with the reduction of the BI and II, and an increased in the PML. FIG. 1 shows the clinical aspects on the implants at the baseline and after 10 days of the beginning of the use of the exemplary dentifrice oral compositions of the present invention. Tables 1 and 2 show the periimplant parameters at the baseline and after 10 days of the beginning of the use of the exemplary dentifrice oral composition of the present invention. Table 3 shows the mean and standard deviation of the periimplant parameters at baseline and after 10 days of the beginning of the use of the dentifrice.

TABLE 1

Baseline parameters of the patients that used the exemplary dentifrice oral composition

| Patient | Number of Implants | Location | PB | PML | CAL | BI | II |
| --- | --- | --- | --- | --- | --- | --- | --- |
| 1 | 2 | 36, 37 | 0.33 | 0.58 | 0.91 | 1.66 | 2.08 |
| 2 | 5 | 14, 12, 11, 22, 24 | 2.2 | −0.90 | 1.30 | 1.23 | 1.50 |
| 3 | 2 | 36, 37 | 1.83 | 1.16 | 3.00 | 2.08 | 1.83 |
| 4 | 3 | 13, 36, 45 | 1.33 | −0.05 | 1.27 | 0.33 | 0.50 |
| 5 | 5 | 15, 12, 22, 25, 27 | 1.70 | 0.06 | 1.76 | 0.00 | 0.33 |
| 6 | 4 | 15, 25, 35, 36 | 1.29 | 0.00 | 1.29 | 0.70 | 1.00 |
| 7 | 6 | 15, 14, 26, 27, 35, 37 | 2.11 | 0.33 | 2.44 | 1.41 | 1.08 |
| 8 | 8 | 16, 14, 24, 25, 26, 34, 35, 45 | 1.29 | 0.06 | 1.35 | 0.75 | 0.89 |
| 9 | 9 | 14, 11, 21, 24, 35, 36, 45, 46, 47 | 1.18 | 0.04 | 1.22 | 0.48 | 0.77 |
| 10 | 4 | 16, 14, 12, 22 | 1.00 | −0.37 | 0.62 | 0.95 | 1.16 |

PB-Probing depth; PML-Periimplant mucosal level; CAL-Clinical attachment level; BI-Biofilm index; II-Inflammation index.

TABLE 2

Periimplant parameters of the patients after 10 days of the use of the exemplary dentifrice oral composition

| Patient | Number of Implants | Location | PB | PML | CAL | BI | II |
| --- | --- | --- | --- | --- | --- | --- | --- |
| 1 | 2 | 36, 37 | 0.40 | 0.55 | 0.95 | 0.00 | 0.00 |
| 2 | 5 | 14, 12, 11, 22, 24 | 1.85 | −0.22 | 1.63 | 0.13 | 0.63 |
| 3 | 2 | 36, 37 | 1.81 | 1.30 | 3.11 | 0.66 | 1.16 |
| 4 | 3 | 13, 36, 45 | 1.30 | 0.00 | 1.30 | 0.44 | 0.11 |
| 5 | 5 | 15, 12, 22, 25, 27 | 1.75 | 0.10 | 1.85 | 0.00 | 0.00 |

TABLE 2-continued

Periimplant parameters of the patients after 10 days of the use of the exemplary dentifrice oral composition

| Patient | Number of Implants | Location | PB | PML | CAL | BI | II |
|---|---|---|---|---|---|---|---|
| 6 | 4 | 15, 25, 35, 36 | 1.16 | 0.00 | 1.16 | 0.33 | 0.25 |
| 7 | 6 | 15, 14, 26, 27, 35, 37 | 2.03 | 0.45 | 2.48 | 1.27 | 1.47 |
| 8 | 8 | 16, 14, 24, 25, 26, 34, 35, 36, 45 | 1.25 | 0.15 | 1.40 | 0.04 | 0.35 |
| 9 | 9 | 14, 11, 21, 24, 35, 36, 45, 46, 47 | 1.20 | 0.18 | 1.28 | 0.24 | 0.37 |
| 10 | 4 | 16, 14, 12, 22 | 1.00 | −0.05 | 0.95 | 0.33 | 0.66 |

PB-Probing depth; PML-Periimplant mucosal level; CAL-Clinical attachment level; BI-Biofilm index; II-Inflammation index.

TABLE 3

Mean and standard deviation of the periimplant parameters at baseline and after 10 days of the beginning of the use of exemplary dentifrice oral composition

| Parameter/Period | Baseline | After 10 days |
|---|---|---|
| PB | 1.42 ± 0.55 | 1.37 ± 0.49 |
| PML | 0.09 ± 0.54 | 0.24 ± 0.43* |
| CAL | 1.51 ± 0.71 | 1.61 ± 0.69 |
| BI | 0.95 ± 0.63 | 0.34 ± 0.38# |
| II | 1.11 ± 0.55 | 0.50 ± 0.49# |

PB-Probing depth; PML-Periimplant mucosal level; CAL-Clinical attachment level; BI-Biofilm index; II-Inflammation index.
*Higher values than the baseline; #Lower values than the baseline-Paired t-test ($p < 0.05$).

Gel 11 patients were treated with partial fixed prothesis supported by implants. These patients had a total 64 implants. Only one patient experienced a baseline CAL of 3 mm (patient 8). It was showed that all the patients experienced a reduction in the BI and II. In general, the use of the exemplary gel oral composition of the present invention was associated with the reduction of the BI and II, and an increased in the PML. Tables 4 and 5 show the periimplant parameters at the baseline and after 10 days of the beginning of the use of the exemplary gel oral composition of the present invention. Table 6 shows the mean and standard deviation of the periimplant parameters at baseline and after 10 days of the beginning of the use of the exemplary gel oral composition of the present invention.

TABLE 4

Baseline parameters of the patients that used the exemplary gel oral composition

| Patient | Number of Implants | Location | PB | PML | CAL | BI | II |
|---|---|---|---|---|---|---|---|
| 1 | 8 | 24, 25, 34, 35, 36, 44, 45, 46 | 2.27 | 0.12 | 2.39 | 0.56 | 0.54 |
| 2 | 7 | 25, 11, 34, 35, 36, 45, 46 | 1.23 | 0.14 | 1.38 | 0.92 | 0.83 |
| 3 | 9 | 16, 14, 24, 25, 26, 34, 35, 36, 45 | 1.40 | 0.38 | 1.79 | 0.72 | 0.85 |
| 4 | 2 | 45, 46 | 0.83 | 0.00 | 0.83 | 0.08 | 0.33 |
| 5 | 2 | 43, 44 | 0.25 | 0.00 | 0.25 | 0.50 | 0.75 |
| 6 | 5 | 33, 34, 36, 44, 46 | 1.16 | 0.93 | 2.10 | 1.26 | 1.30 |
| 7 | 10 | 17, 16, 22, 24, 25, 26, 36, 37, 46, 47 | 1.88 | 0.05 | 1.93 | 0.86 | 1.00 |
| 8 | 3 | 24, 25, 26 | 3.00 | 0.00 | 3.00 | 0.77 | 1.83 |
| 9 | 2 | 36, 46 | 0.75 | 0.08 | 0.83 | 0.25 | 0.25 |
| 10 | 12 | 14, 12-22, 24, 26, 27, 34, 35, 44, 46 | 1.41 | 0.88 | 2.30 | 1.15 | 1.44 |
| 11 | 4 | 33, 31, 41, 43 | 1.04 | 1.37 | 2.41 | 1.91 | 1.33 |

PB-Probing depth; PML-Periimplant mucosal level; CAL-Clinical attachment level; BI-Biofilm index; II-Inflammation index.

TABLE 5

Periimplant parameters of the patients after 10 days of the use of the exemplary gel oral composition

| Patient | Number of Implants | Location | PB | PML | CAL | BI | II |
|---|---|---|---|---|---|---|---|
| 1 | 8 | 24, 25, 34, 35, 36, 44, 45, 46 | 2.14 | 0.06 | 2.20 | 0.14 | 0.35 |
| 2 | 7 | 25, 11, 34, 35, 36, 45, 46 | 1.20 | 0.22 | 1.42 | 0.33 | 0.09 |
| 3 | 9 | 16, 14, 24, 25, 26, 34, 35, 36, 45 | 1.36 | 0.55 | 1.91 | 0.22 | 0.42 |
| 4 | 2 | 45, 46 | 0.58 | 0.00 | 0.58 | 0.00 | 0.00 |
| 5 | 2 | 43, 44 | 0.16 | 0.00 | 0.16 | 0.00 | 0.00 |
| 6 | 5 | 33, 34, 36, 44, 46 | 1.20 | 1.05 | 2.25 | 0.60 | 0.70 |
| 7 | 10 | 17, 16, 22, 24, 25, 26, 36, 37, 46, 47 | 1.98 | 0.06 | 2.04 | 0.50 | 0.63 |
| 8 | 3 | 24, 25, 26 | 2.55 | 0.00 | 2.55 | 0.27 | 1.22 |

TABLE 5-continued

Periimplant parameters of the patients after 10 days of the use of the exemplary gel oral composition

| Patient | Number of Implants | Location | PB | PML | CAL | BI | II |
|---|---|---|---|---|---|---|---|
| 9 | 2 | 36, 46 | 0.66 | 0.16 | 0.83 | 0.00 | 0.00 |
| 10 | 12 | 14, 12-22, 24, 26, 27, 34, 35, 44, 46 | 1.39 | 1.03 | 2.42 | 0.75 | 0.80 |
| 11 | 4 | 33, 31, 41, 43 | 1.15 | 1.45 | 2.60 | 1.04 | 0.83 |

PB-Probing depth; PML-Periimplant mucosal level; CAL-Clinical attachment level; BI-Biofilm index; II-Inflammation index.

TABLE 6

Mean and standard deviation of the periimplant parameters at baseline and after 10 days of the beginning of the use of the exemplary gel oral composition

| Parameter/Period | Baseline | After 10 days |
|---|---|---|
| PB | 1.38 ± 0.76 | 1.30 ± 0.70 |
| PML | 0.35 ± 0.47 | 0.41 ± 0.52* |
| CAL | 1.74 ± 0.83 | 1.72 ± 0.84 |
| BI | 0.81 ± 0.50 | 0.35 ± 0.34# |
| II | 0.95 ± 0.48 | 0.45 ± 0.41# |

PB-Probing depth; PML-Periimplant mucosal level; CAL-Clinical attachment level; BI-Biofilm index; II-Inflammation index.
*Higher values than the baseline; #Lower values than the baseline-Paired t-test ($p < 0.05$).

Figure 2:
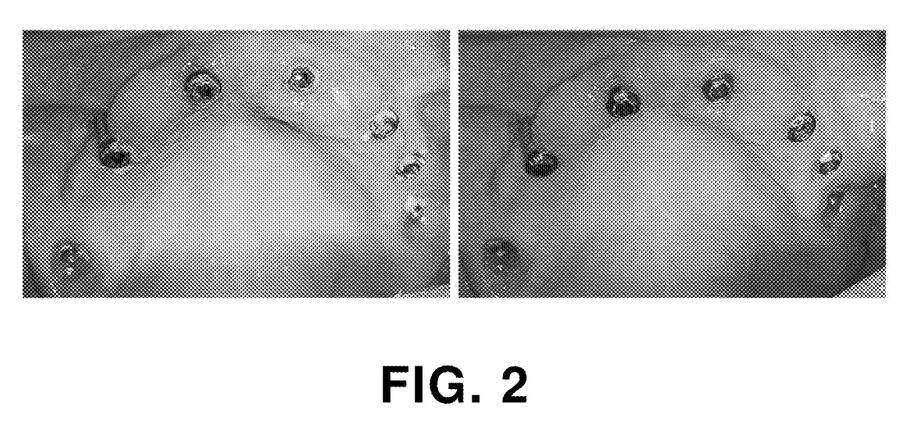
FIG. 2 the clinical aspect at the baseline (left) and after (right) the use for 10 days of an exemplary mouthwash oral composition of the present invention.

Mouthwash 11 patients were treated with total fixed prothesis supported by implants. These patients had a total of 75 implants, 6 lower total fixed prothesis and 7 upper total fixed prothesis. Two patients experienced a baseline CAL higher than 3 mm (patient 5 and 9). It was showed that all patients experienced a reduction in the BI and II, except patient number 10. In general, the use of the exemplary mouthwash oral composition of the present invention was associated with the reduction of the BI and II, and an increased in the PML and CAL. FIG. 2 shows the clinical aspects on the implants at the baseline and after 10 days of the beginning of the use of the exemplary mouthwash oral compositions of the present invention Tables 7 and 8 show the periimplant parameters at the baseline and after 10 days of the beginning of the use of the exemplary mouthwash oral composition of the present invention. Table 9 shows the mean and standard deviation of the periimplant parameters at baseline and after 10 days of the beginning of the use of the exemplary mouthwash oral composition of the present invention.

TABLE 7

Baseline parameters of the patients that used the exemplary mouthwash oral composition

| Patient | Number of Implants | Location | PB | PML | CAL | BI | II |
|---|---|---|---|---|---|---|---|
| 1 | 5 | Mandible | 1.36 | 1.96 | 3.33 | 3.00 | 2.20 |
| 2 | 4 | Maxilla | 0.79 | 0.00 | 0.79 | 1.20 | 0.54 |
| 3 | 5 | Mandible | 1.20 | 0.60 | 1.80 | 1.20 | 0.30 |
| 4 | 8 | Maxilla | 1.72 | −0.77 | 0.95 | 0.97 | 1.81 |
| 5 | 7 | Maxilla | 2.66 | 1.73 | 4.40 | 2.02 | 2.45 |
| 6 | 12 | Mandible/Maxilla | 0.87 | −0.30 | 0.59 | 0.41 | 0.29 |
| 7 | 11 | Mandible/Maxilla | 2.71 | 0.19 | 2.90 | 2.31 | 2.45 |
| 8 | 7 | Maxilla | 1.85 | 0.52 | 2.30 | 2.76 | 1.80 |
| 9 | 4 | Mandible | 1.70 | 1.41 | 3.12 | 1.75 | 1.70 |
| 10 | 4 | Mandible | 1.29 | 0.25 | 1.54 | 1.79 | 1.04 |
| 11 | 8 | Maxilla | 1.27 | 0.00 | 1.27 | 1.79 | 1.50 |

PB-Probing depth; PML-Periimplant mucosal level; CAL-Clinical attachment level; BI-Biofilm index; II-Inflammation index.

TABLE 8

Periimplant parameters of the patients after 10 days of the use of the exemplary mouthwash oral composition

| Patient | Number of Implants | Location | PB | PML | CAL | BI | II |
|---|---|---|---|---|---|---|---|
| 1 | 5 | Mandible | 1.30 | 2.10 | 3.40 | 0.66 | 0.13 |
| 2 | 4 | Maxilla | 0.65 | 0.00 | 0.65 | 0.29 | 0.12 |
| 3 | 5 | Mandible | 1.26 | 0.68 | 1.94 | 0.56 | 0.93 |
| 4 | 8 | Maxilla | 1.72 | −0.14 | 1.58 | 0.43 | 0.64 |
| 5 | 7 | Maxilla | 2.87 | 1.81 | 4.68 | 1.14 | 1.14 |
| 6 | 12 | Mandible/Maxilla | 0.81 | −0.09 | 0.72 | 0.00 | 0.00 |
| 7 | 11 | Mandible/Maxilla | 2.87 | 0.28 | 3.15 | 1.06 | 0.93 |
| 8 | 7 | Maxilla | 2.04 | 0.60 | 2.64 | 0.59 | 0.42 |
| 9 | 4 | Mandible | 1.90 | 1.55 | 3.45 | 1.29 | 0.87 |
| 10 | 4 | Mandible | 1.50 | 0.40 | 1.90 | 1.79 | 0.79 |
| 11 | 8 | Maxilla | 1.15 | 0.00 | 1.15 | 0.95 | 0.27 |

PB-Probing depth; PML-Periimplant mucosal level; CAL-Clinical attachment level; BI-Biofilm index; II-Inflammation index.

TABLE 9

Mean and standard deviation of the periimplant parameters at baseline and after 10 days of the beginning of the use of the exemplary mouthwash oral composition

| Parameter/Period | Baseline | After 10 days |
|---|---|---|
| PB | 1.58 ± 0.63 | 1.64 ± 0.73 |
| PML | 0.50 ± 0.85 | 0.65 ± 0.80* |
| CAL | 2.09 ± 1.22 | 2.29 ± 1.28* |
| BI | 1.74 ± 0.77 | 0.79 ± 0.50# |
| II | 1.46 ± 0.80 | 0.56 ± 0.39# |

PB-Probing depth; PML-Periimplant mucosal level; CAL-Clinical attachment level; BI-Biofilm index; II-Inflammation index.
*Higher values than the baseline; #Lower values than the baseline-Paired t-test ($p < 0.05$).

Conclusions

According to the results of this short-term clinical laboratory study test, the oral compositions of the present invention led to:

1. A showing of promising results in the health of soft tissue around dental implants;
2. A reduction in the biofilm index in all groups treated with the oral compositions of the present invention embodied in the different vehicles outlined above;
3. A reduction in the inflammation index for all the groups treated with the oral compositions of the present invention embodied in the different vehicles outlined above;
4. A showing of no signs of undesirable side effects.

More specific and exemplary embodiments of the oral compositions of the present invention are also shown in Examples D, E and F.

In yet another specific and preferred embodiment, an oral composition of the present invention in gel form is shown below. This composition is made using conventional methods.

Example D

| Active Ingredient | Gel | Function |
| --- | --- | --- |
| Carboximetilcelullose | 1.00 | Thickener |
| Glycerin | 5.00 | Humectant |
| Sorbitol | 60.00 | Humectant |
| Sodium Benzoate | 0.30 | Preservative |
| Xilitol | 0.50 | Sweetener/Anticavity |
| Lauryl Glucoside | 1.50 | Nonionic Tensoactive |
| Sodium Lauryl Sulfate | 0.50 | Anionic Tensoactive |
| Hyaluronic Acid | 0.05 | Mucus Regenerator |
| Polyvinylpyrrolidone K30 | 0.50 | Film Forming Agent |
| Dimethyl silanediol salicylate | 0.50 | Antiseptic and Mucus Regenerator |
| Tixosil ® 43 B | 10.00 | Thickener and Thixotropic Agent |
| Tixosil ® 73 | 5.00 | Abrasive |
| Tetrasodium pyrophosphate | 0.50 | Anti-tartar |
| Saccharin | 0.05 | Sweetener |
| Camelia Sinensis (Green Tea Extract) | 0.50 | Antioxidant, Antiseptic |
| Hydrogenated Ricinus Oil (Castor Oil) | 2.00 | Solubilizer, Solubilizing Agent |
| Mint Aroma | 0.60 | Flavoring |
| EDTA | 0.05 | Chelating Agent |
| Blue Dye Cl42090 | q.s. | Colorant |
| Yello Dye Cl 19140 | q.s. | Colorant |
| Purified Water | 11.45 | Vehicle |

In another specific and preferred embodiment, an oral composition of the present invention in dentrifice form is shown below. This composition is made using conventional methods.

Example E

| Active Ingredient | Dentrifice | Function |
| --- | --- | --- |
| Carboximetilcelullose | 1.20 | Thickener |
| Glycerin | 40.00 | Humectant |
| Sodium Benzoate | 0.30 | Preservative |
| Xilitol | 0.50 | Sweetener/Anticavity |
| Lauryl Glucoside | 1.50 | Nonionic Tensoactive |
| Sodium Lauryl Sulfate | 0.50 | Anionic Tensoactive |
| Hyaluronic Acid | 0.05 | Mucus Regenerator |
| Titanium Dioxide | 1.00 | Coloring |
| Polyvinylpyrrolidone K30 | 0.50 | Film Forming Agent |
| Dimethylsilanediol salicylate | 0.50 | Antiseptic and Mucus Regenerator |
| Tixosil ® 43 B | 10.00 | Thickener and Thixotropic Agent |
| Tixosil ® 73 | 10.00 | Abrasive |
| Tetrasodium pyrophosphate | 0.50 | Anti-tartar |
| Saccharin | 0.10 | Sweetener |
| Camelia Sinensis (Green Tea Extract) | 0.50 | Antioxidant, Antiseptic |
| Hydrogenated Ricinus Oil (Castor Oil) | 2.00 | Solubilizer, Solubilizing Agent |
| Mint Aroma | 0.60 | Flavoring |
| EDTA | 0.05 | Chelating Agent |
| Purified Water | 30.20 | Vehicle |

In yet another specific and preferred embodiment, an oral composition of the present invention in mouthwash form is shown below. This composition is made using conventional methods.

Example F

| Active Ingredient | Mouthwash | Function |
| --- | --- | --- |
| Glycerin | 20.00 | Humectant |
| Sodium Benzoate | 0.30 | Preservative |
| Xilitol | 0.50 | Sweetener/Anticavity |
| Lauryl Glucoside | 1.50 | Nonionic Tensoactive |
| Sodium Lauryl Sulfate | 0.50 | Anionic Tensoactive |
| Hyaluronic Acid | 0.05 | Mucus Regenerator |
| Polyvinylpyrrolidone K30 | 0.50 | Film Forming Agent |
| Dimethylsilanediol salicylate | 0.50 | Antiseptic and Mucus Regenerator |
| Tetrasodium pyrophosphate | 0.50 | Anti-tartar |
| Saccharin | 0.05 | Sweetener |
| Camelia Sinensis (Green Tea Extract) | 0.50 | Antioxidant, Antiseptic |
| Hydrogenated Ricinus Oil (Castor Oil) | 2.00 | Solubilizer, Solubilizing Agent |
| Mint Aroma | 0.30 | Flavoring |
| EDTA | 0.05 | Chelating Agent |
| Blue Dye Cl42090 | q.s. | Colorant |
| Yellow Dye Cl19140 | q.s. | Colorant |
| Purified Water | 72.75 | Vehicle |

The values disclosed and specified in all of the Examples herein are not to be understood as being strictly limited to the exact numerical values recited. Instead, unless otherwise specified, each value is intended to mean both the recited value and a functionally equivalent range surrounding that value.

To evaluate the efficacy and safety in clinical application of the oral compositions of the present invention specified in Examples D, E and F, a protocol was established based on the comparison of a commercially available dentifrice and those oral compositions of the present invention.

A group of 10 patients used the implant dentifrices/oral compositions of the present invention of Examples D, E and F, with brushing according to the Bass recommended technique. Other 10 patients employed the same technique using the commercially available dentifrice.

After a 10-day period of use of the oral compositions of the present invention and the commercially available dentifrice, it was found that the use of the oral compositions/dentifrices of the present invention exemplified in Examples D, E and F for implanted teeth had the following characteristics and yielded the following results:

(a) Marked improvement of the quality of the highly keratinized gingival tissue;
(b) Bad breath reduction, which was measured by a Halimeter;
(c) Improvement and quickness of healing of the implanted area;
(d) Sharp decrease in gingival index measured by the depth of the groove, as well as bleeding;
(e) Sensible reduction in plaque build-up visualized with application of the novel and revealing oral composition of the present invention.

With the previously made observations deriving from the oral compositions of the present invention comparison study, the following conclusions were reached:

I. The oral compositions of the present invention embodied and exemplified in Examples D, E and F have a polishing and sanitizing system constituted by the thixotropic abrasive silica Tixosil® 73 in the 5% ratio.

II. The oral compositions of the present invention embodied and exemplified in Examples D, E and F have its long-acting properties/powers due to the presence of Polyvinyl pyrrolidone K30.

III. The oral compositions of the present invention embodied and exemplified in Examples D, E and F have a surfactant system using lauryl glucoside (non-ionic surfactant) responsible for chemical sanitization, foaming, mucosal hydration and cell membrane protection—these properties protecting the mucosa.

IV. The oral compositions of the present invention embodied and exemplified in Examples D, E and F have a thickener system using carboxymethylcellulose and silica (Tixosil® 43B), which provides rheological behavior responsible for the good stability of the oral composition and release of the actives during brushing.

V. The oral compositions of the present invention embodied and exemplified in Examples D, E and F have a component with a mucosal regenerating action responsible for speeding the process of healing or tissue regeneration—D.S.B.C.® as the commercially available Silanol salicylate, a silanol that also prevents atrophy of the bone structure.

VI. The oral compositions of the present invention embodied and exemplified in Examples D, E and F shows the green tea extract component with anti-inflammatory properties, antioxidant, and anti-bactericide.

VII. The oral compositions of the present invention embodied and exemplified in Examples D, E and F have the hyaluronic acid component, a mucous regenerator with anti-inflammatory and anti-inflammatory properties.

VIII. The oral compositions of the present invention embodied and exemplified in Examples D, E and F have a complex composition, but all its components and actives thereof are perfectly compatible and synergistic and have contributed to the health and consequently increased longevity of dental implants.

What is claimed is:

1. An oral composition, comprising:
   one or more mucus regenerators, wherein the one or more mucus regenerators comprises hyaluronic acid;
   one or more antiseptic agents, wherein the one or more antiseptic agents comprises green tea extract present in an effective amount of about 0.50% to about 1.00%, by total weight of the composition;
   silanol salicylate, present in an effective amount of about 0.50% by total weight of the composition; and
   one or more orally acceptable carrier actives selected from the group consisting of one or more thickeners, one or more humectants, one or more sweeteners, a preservative, one or more surfactants, a film forming agent, a thixotropic agent, a solubilizing agent, a chelating agent, a coloring agent, an anti-tartar agent, an abrasive, an antioxidant agent, a flavoring agent, a water vehicle, and mixtures thereof.

2. The oral composition of claim 1, wherein the one or more mucus regenerators are present in an effective amount of about 0.05% to about 0.55%, by total weight of the composition.

3. The oral composition of claim 1, wherein the one or more thickeners is carboxymethyl cellulose, a thickening silica, or mixtures thereof, and wherein the one or more thickeners are present in an effective amount of about 1.00% to about 11.20%, by total weight of the composition.

4. The oral composition of claim 1, wherein the one or more humectants is glycerin, sorbitol, or mixtures thereof, and wherein the one or more humectants are present in an effective amount of about 5.00% to about 65.00%, by total weight of the composition.

5. The oral composition of claim 1, wherein the one or more sweeteners is xylitol, saccharin, or mixtures thereof, and wherein the one or more humectants are present in an effective amount of about 0.05% to about 0.60%, by total weight of the composition.

6. The oral composition of claim 1, wherein the one or more surfactants is lauryl glucoside, lauryl sodium sulfate, or mixtures thereof, and wherein the one or more surfactants are present in an effective amount of about 0.50% to about 2.00%, by total weight of the composition.

7. The oral composition of claim 1, wherein the abrasive is an abrasive silica, and wherein the abrasive is present in an effective amount of about 5.00% to about 10.00%, by total weight of the composition, wherein the film forming agent is polyvinylpyrrolidone K30, and wherein the film forming agent is present in an effective amount of about 0.50%, by total weight of the composition.

8. The oral composition of claim 1, wherein the thixotropic agent is a thickening silica, and wherein the thixotropic agent is present in an effective amount of about 10.00%, by total weight of the composition.

9. The oral composition of claim 1, wherein the anti-antioxidant agent is green tea extract, and wherein the antioxidant agent is present in an effective amount of about 0.50%, by total weight of the composition.

10. The oral composition of claim 1, wherein the preservative is sodium benzoate, and wherein the preservative is present in an effective amount of about 0.30%, by total weight of the composition, wherein the solubilizing agent is hydrogenated ricinus oil, and wherein the solubilizing agent is present in an effective amount of about 2.00%, by total weight of the composition, wherein the chelating agent is ethylenediaminetetraacetic acid (EDTA), and wherein the chelating agent is present in an effective amount of about 0.05%, by total weight of the composition, wherein the water vehicle is purified water, and wherein the water vehicle is present in an effective amount of about 11% to about 73%, by total weight of the composition.

11. The oral composition of claim 1, wherein the coloring agent is titanium dioxide, and wherein the coloring agent is present in an effective amount of about 1.00%, by total weight of the composition, wherein the flavoring agent is mint aroma, and wherein the flavoring agent is present in an effective amount of about 0.30 to about 0.60%, by total weight of the composition.

12. The oral composition of claim 1, wherein the anti-tartar agent is tetrasodium pyrophosphate, and wherein the anti-tartar agent is present in an effective amount of about 0.50%, by total weight of the composition, wherein the anti-cavity agent is xylitol, and wherein the anti-cavity agent is present in an effective amount of about 0.50%, by total weight of the composition.

13. The oral composition of claim 1, wherein the oral composition is a mouthwash, dentifrice, toothpaste, tooth gel, tooth powder, non-abrasive gel, subgingival gel, petrolatum gel, mousse, foam, mouth spray, lozenge, lipstick, prophy paste, chewing gum, oral tablet, sponge, floss, or dental implement, or may be incorporated onto strips or films for direct application or attachment to oral surfaces.

14. The oral composition of claim 1, wherein the oral composition is suitable to be used and associated with a condition selected from the group consisting of: tooth loss, oral surgery, endodontic pathoses, stomatitis, alveolar bone resorption, lesions, gingivitis, periodontitis, tobacco induced disease, and combinations thereof.

* * * * *